(12) United States Patent
Muta et al.

(10) Patent No.: US 7,045,137 B1
(45) Date of Patent: May 16, 2006

(54) SHEET-TYPE PACKS

(75) Inventors: Kazunori Muta, Saga (JP); Yasuhisa Kose, Saga (JP); Shigehiro Oishi, Saga (JP); Tomoyuki Hinotani, Saga (JP)

(73) Assignee: Hisamitsu Pharmaceuticals Co., Inc., Saga (JP)

( * ) Notice: Subject to any disclaimer, the term of this patent is extended or adjusted under 35 U.S.C. 154(b) by 0 days.

(21) Appl. No.: 09/890,224

(22) PCT Filed: Jan. 28, 2000

(86) PCT No.: PCT/JP00/00459

§ 371 (c)(1),
(2), (4) Date: Jul. 27, 2001

(87) PCT Pub. No.: WO00/44336

PCT Pub. Date: Aug. 3, 2000

(30) Foreign Application Priority Data

Jan. 28, 1999 (JP) ............................. 11-019428

(51) Int. Cl.
*A61K 7/00* (2006.01)
*A61K 9/00* (2006.01)

(52) U.S. Cl. ....................... 424/400; 424/401
(58) Field of Classification Search ................. 424/401, 424/448, 449, 402
See application file for complete search history.

(56) References Cited

U.S. PATENT DOCUMENTS 5,578,312 A  11/1996 Parrinello

FOREIGN PATENT DOCUMENTS

| EP | 1151749 A1 | 11/2001 |
|---|---|---|
| FR | 2719473 A | 11/1995 |
| FR | 2734574 A | 11/1996 |
| GB | 2321587 A | 8/1998 |
| JP | 54-49334 A | 4/1979 |
| JP | 60-115507 A | 6/1985 |
| JP | 03080867 | 4/1991 |
| JP | 5-295004 A | 11/1993 |
| JP | 08040882 A | 2/1996 |
| JP | 08188527 A | 7/1996 |
| JP | 10053527 | 2/1998 |
| JP | 3053730 U | 8/1998 |
| JP | 11269031 A | 10/1999 |
| WO | WO 93 25186 A | 12/1993 |

OTHER PUBLICATIONS

Database EPODOC 'Online, European Patent Office, The Hague, NL; Database accession No. kr9615183 XP002240815 Abstract & KR 9615183B Nov. 1, 1996.

Database EPODOC 'Online! European Patent Office, The Hague, NL; Database accession No. kr9615185 XP002240816 Abstract & KR 9615185B Nov. 1, 1996.

*Primary Examiner*—Thurman K. Page
*Assistant Examiner*—Sharon L. Howard
(74) *Attorney, Agent, or Firm*—Wolf, Greenfield & Sacks, P.C.

(57) ABSTRACT

Sheet-type packs which exert a skin cleaning effect while maintaining an effect of appropriately moistening the skin and are excellent in the feel in using and safety to the skin. In particular, sheet-type packs containing fruit extracts.

11 Claims, No Drawings

SHEET-TYPE PACKS

RELATED APPLICATIONS

This application is a national stage filing under 35 U.S.C. 0317 of PCT application PCT/JP00/00459, filed Jan. 28, 2000. Foreign priority benefits are claimed under 35 U.S.C. §119(a)–(d) or 35 U.S.C. §365(b) of Japan application number 11-19428, filed Jan. 28, 1999.

TECHNICAL FIELD

The invention relates to a sheet-shaped pack agent. More specifically, it relates to a sheet-shaped pack agent giving a wet feeling to the skin which is suitable for a cosmetics or a quasi-drug used for skindressing and beauty.

BACKGROUND ART

As a pack preparation, a pack having an excellent water holding capacity and a low removal strength, which contains polyacrylates, polyhydric alcohols and water as its main components, is described in JP, A, 54-49334. Also, in JP, B, 1-46485, a sheet-shaped pack agent using a cross-linking type aqueous gel as a base material, and further in JP, A, 5-295004, a pack mixed with a naturally derived semisynthetic component as a moisturising agent and a thickener are disclosed.

However, a conventional pack has a tendency to lack water supply and moisturising effect for the skin or it tends not to release a moisturising component; and consequently, it has the problem that a pack effect for the skin is not sufficient.

DISCLOSURE OF THE INVENTION

Thus the problem to be solved by the invention is to provide a sheet-shaped pack against which solves the above conventional problems, shows a beauty-skin effect keeping an appropriate moisture to skin and still has a pack effect excellent in usability and safety for the skin.

The inventors made extensive research to solve the above problems and found out their solution.

Namely, the invention relates to a sheet-shaped pack agent containing a fruit extract.

A sheet-shaped pack agent of the invention essentially consists of a base agent and a base fabric e.g. a nonwoven fabric. The base agent usually contains a moisturising agent, a water soluble polymer, a cross-linking agent and water, and further this can appropriately contain an antiseptic, a beauty-skin auxiliary component (for example, dipotassium glycyrrhizinate, horse chestnut extract, allantoin, water soluble placenta extract, clove oil, sage oil or the like), antioxidant, an adhesiveness donating agent, dissolution agent, color, perfume, surfactant, UV absorber, an inorganic filler, a pH adjusting agent etc. in a suitable amount.

Also, in a sheet-shaped pack agent of the invention it is preferable that the density of a fruit extract is 0.95–1.20, the pH is 3.3–5.0 and the sugar content is 19–23% by weight.

Further, in a sheet-shaped pack agent of the invention, the mix proportion of a fruit extract in a total amount of a base agent is preferably 0.0003–33.87 wt. % and the proportion of the fruit extract in a total amount of a moisturising agent is preferably 0.03–96.77 wt. %. It is preferable that the base agent consists of a moisturising agent 1–35 wt. %, a water soluble polymer 3–25 wt. %, a cross-linking agent 0.05–20 wt. %, water 60–95 wt. % and an antiseptic 0.005–10 wt. %.

Also, a sheet-shaped pack agent of the inventory may further contain a glycol in addition to a fruit extract. In this case, the mix ratio of the glycol to the fruit extract is preferably 1 . 35:0.01–30, and the glycol is preferably polyethylene glycol and/or polypropylene glycol.

In the invention, a fruit extract is one or more species of fruit extracts selected from the group comprising rose fruit extract, orange extract, orange juice, raspberry extract, kiwi extract, cucumber extract, gardenia extract, grapefruit extract, crataegus fruit extract, Japanese pepper extract, crataegus extract, common juniper extract, jujube extract, duke extract, tomato extract, grape extract, loofah extract, lime juice, apple extract, apple juice, lemon extract or lemon juice.

Further, according to the invention are provided cosmetics for the skin cosmetic or a quasi-drug using the above sheet-shaped pack agent.

DETAILED DESCRIPTION OF PREFERRED EMBODIMENT

In the following, the embodiment of a sheet-shaped pack agent according to the invention will be explained in more details, but it is to be understood that the invention is not limited thereby in any way.

In the invention, the fruit extract is contained in a moisturising agent and is one in which fruit and/or pericarp are extracted by either one or a mixture of not less than two from water, ethanol, propylene glycol, 1,3-butylene glycol and polyethylene glycol. Expediently are mixed one or more species from rose fruit extract, orange extract, orange juice, raspberry extract, kiwi extract, cucumber extract, gardenia extract, grape fruit extract, crataegus fruit extract, Japanese pepper extract, crataegus extract, common juniper extract, jujube extract, duke extract, tomato extract, grape extract, loofah extract, lime juice, apple extract, apple juice, lemon extract or lemon juice. These fruit extracts are appropriately mixed in a suitable amount, though they are mixed preferably in 0.0003–33.87 wt. %, more preferably in 0.0025–20 wt. %. Here, the proportion of the fruit extract in a total amount of a moisturising agent is 0.03–96.77 wt. %, preferably 0.04–83.33 wt. %, more preferably 0.05–80.00 wt. %, and it is more preferable to let the sheet-shaped pack agent contain the fruit extract or the mixture of more than two fruit extracts whose density is made in the range of 0.95–1.20, preferably 0.98–1.10, and the pH is in the range of 3.3–5.0, preferably 3.5–4.0, and further sugar content is in the range of 19–23 wt. %, preferably 20–22 wt. %, and the kinetic viscosity (25° C.) is in the range of 2.3–2.8 $mm^2/S$, preferably 2.5–2.7 $mm^2/S$, the vitamin C (ascorbic acid) content is not less than 10.0μ g, because the irritancy toward the skin is more alleviated, and not only a relaxant effect by a soft aroma but a beauty-skin effect is brought extremely better. Also, the fruit extract has an effect as perfume by the fragrance peculiar to each extract.

Further, as a glycol used likewise as a moisturising agent in the invention, polyethylene glycol and/or polypropylene glycol, in particular polyethylene glycol of the average molecular weight 200–600, polypropylene glycol of the average molecular weight 500–3000, and the like having an polyether structure are preferable, and one or more species of these can be used by mixing.

The mix amount of these moisturising agents based on a total amount of a base agent is determined considering an adhesiveness and agglutinativeness of a preparation, a water holding-capacity and a shape retaining property before use, uniformity of gel, workability, usability at the time of use, and the like, though it is preferably 1–35 wt. %, more preferably 5–30 wt. %, and furthermore preferably 5–25 wt. %.

On the other hand, the mix proportion of the moisturising agents consisting of two components of the glycol and the fruit extract is also determined considering an adhesiveness and agglutinativeness of a preparation, a water holding capacity and a shape retaining property before use, uniformity of gel, workability, usability at the time of use, further a skin-beauty effect by vitamin C and α-hydroxy acid contained in the fruit extract, and a soft and refreshing effect by a faint fragrance of the fruit extract, and the like, though it is preferably in the range of 1–35:0.01–30, more preferably 5–25:0.01 . 25, and furthermore preferably 5–20:0.01–20.

A pack containing a moisturising agent consisting of the glycol and the fruit extract is preferably prepared so that said moisturising agent is in a mix amount of 5–25 wt. %, and a mix proportion of the glycol and the fruit extract contained therein is in the range of 5–20:0.01–2.0. Here, the proportion of the glycol is the total moisturising agent is in the range of 3.23–99.97 wt. %, preferably 16.67–99.96 wt. %, and more preferably 20.00–99.95 wt. %.

Illustrative of the aqueous polymers are gelatin, polyacrylic acids, salts thereof or partial neutralization products thereof or the like, and each can be used individually or by mixing more than two species. As salts of polyacrylate, metal salts such as sodium, lithium and potassium are preferable, and one whose average degree of polymerization is 1000–100000 is expediently used. The mixing amount of these aqueous polymers is determined in consideration of an adhesiveness and agglutinativeness of a preparation, a shape retaining property, water absorption, non-uniformity of adhesive mass, lowering of workability, lowering or usability, and the like. However, it is usually used in the range of preferably 3 . 25 wt. %, more preferably 5–20 wt. %, and yet more preferably 5–10 wt. %.

As the cross-linking agent, a water slight soluble aluminum compound or a polyfunctional epoxy compound can be used by mixing one or more species. Illustrative of the water slight soluble aluminum compounds are aluminum hydroxide, aluminum silicate hydrate, synthetic aluminum silicate, kaolin, aluminum acetate, aluminum lactate, aluminum stearate, dry aluminum hydroxide gel, magnesium metasilicate aluminate, magnesium silicate aluminate, aluminum dihydroxy aminoacetate, synthetic hydrotarcite aluminum magnesium silicate and the like, and one or more species of these can be used by mixing. Use of the water slight soluble aluminum compounds gives gel an appropriate strength in an initial physical property as a filler, as well as an inhibitory effect for skin irritancy by the antacid action and a skin astringent action by trace aluminum ion, and along with this aluminum ion dissolves into the preparation in a time course, showing a function to cover the lowering of the gel strength owing to a time dependent decomposition of the polymer and a time dependent cleavage of a cross-linking part of covalent bondings between polymer molecules. Further, the aluminum dissolution rate can be controlled by adjusting pH.

Illustrative of the above polyfunctional epoxy compounds are polyethyleneglycol diglycidyl ether, ethyleneglycol diglycidyl ether, glycerin diglycidyl ether, glycerin triglycidyl ether, propyleneglycol diglycidyl ether, polyglycerol polyglycidyl ether, sorbitol polyglycidyl ether, sorbitan polyglycidyl ether, trimethlolpropane polyglycidyl ether, pentaerythritol polyglycidyl ether, resorcinol diglycidyl ether, neopentylglycol diglycidyl ether, and one or more species of these can be used by mixing. An excellent water absorption and shape retaining property can be obtained by use of the polyfunctional epoxy compounds, and they can produce covalent bonding with the water soluble polymers having a carboxyl, amino or hydroxyl groups, or the like, enhancing a gel strength.

The mix amount of these cross-linking agents is determined considering an agglutinativeness and a shape retaining property of a preparation, lowering of a time dependent stability in a physical property of a preparation, lowering of workability, lowering of safety for the skin, lowering of usability, adhesiveness, an excessive increase of viscosity during production, non-uniformity of adhesive mass by gelation, and the like, though it is 0.05–20 wt. %, preferably 0.5–15 wt. %, and more preferably 1–10 wt. %. Further, considering a mix balance of the moisturising agent, use of the water slight soluble aluminum compound together with the polyfunctional epoxy compound is preferable for a preparation.

As water, a purified water, a sterile water or a natural water are used. Water acts as a dispersion-dissolution agent for the water soluble polymers, the moisturising components, the cross-linking agents, the antiseptics and the like, and especially is important to disperse and dissolute the moisturising agent and the fruit extract uniformly in a preparation. Further, water itself increases usability during the use and after the use, and moves into the skin together with the moisturising agent, bringing an effect to give moisture and tension. Owing to this, the mix amount of water is determined considering an adhesiveness of a preparation, lowering of a water holding capacity before use, lowering of workability, lowering of usability during use, inhibition of adhesiveness and agglutinativeness, lowering of a shape retaining property before use, and the like, though it is added in 60–95 wt. %, preferably 65–90 wt. %, and more preferably 70–85 wt. %. The relative humidity of a preparation itself can be heightened by containing a large amount of water in a preparation, and it becomes possible to drain off effectively a lot of water into the outside, consequently giving moisture to skin and further depriving the heat of vaporization by the evaporation of water into the outside to be able to afford a comfortable refrigerant.

Illustrative of the antiseptics are p-oxybenzoic acid ester (for example, methylparaben, ethylparaben, propylparaben), 1,2-pentanediol, benzoic acid, benzoate, salicylate, sorbic acid, sorbate, dehydroacetate, 4-isopropyl-3-methylphenol, 2-isopropyl-5-methylphenyl, phenol, hinokitiol, cresol, 2,4, 4'-trichloro-2'-hydroxy diphenyl ether, 3,4,4'-trichlorocarbanide, chlorobutanol, benzalkonium chloride and benzethonium chloride, and the other antiseptic known to a person skilled in the art for the purpose, and one or more species of these can be used by mixing. p-Hydroxybenzoic acid ester is preferable among these. The mix amount is determined considering the putrefaction of a preparation by the appearance of molds or bacteria during storage, lowering of usability during use and after use, an unpleasant feeling by adhesiveness, agglutinativeness, irritancy and antiseptic smell in a preparation, and the like, though it is added in 0.005–10 wt. %, preferably 0.01–5 wt. %, and more preferably 0.01–1 wt. %. As a refrigerant or a cold sensation agent, L-methanol, dl-menthol, dl-camphor, eucalyptus oil, mentha oil, isopulegol, 3-L-menthoxypropane-1,2-diol, menthyl pyrrolidonecarboxylate, L-menthyl-3-hydroxybutylate and the like can appropriately be mixed in a suitable amount.

As the antioxidants, can be mixed sodium edetate, ascorbic acid, propyl gallate, butylhydroxyanisol, dibutyl hydroxy toluene, nordihydroguaretic acid, tocopherol, tocopherol acetate and the like.

As the adhesiveness donating agents, can be mixed casein, pullalan, agar, dextran, sodium aluginate, soluble starch, carboxystarch, dextrin, carboxymethyl cellulose, sodium carboxymethyl cellulose, methylcellulose, ethylcellulose, hydroxyethylcellulose, polyvinyl alcohol, polyethylene oxide, polyacrylamide, polyacrylic acid, polyvinylpyrrolidone, carboxyvinyl polymer, polyvinyl ether, polymaleic acid copolymer, methoxyethlene maleicanhydride copolymer, isobutylene maleicanhydride copolymer, polyethlene imine and the like.

As the dissolution agent can be mixed benzyl alcohol, mentha oil, isopropyl mirystate, crotamiton and the like.

As for pigment, it greatly affects the image of a preparation, and one which provide usability and feeling of an activated skin in a greater degree is preferable. Illustrative of the officially designated Coal-tal Color are, for example, Food Red No.2 (Amaranth), Food Red No.3 (Erythrosine), Food Red No.102 (New Coccine), Food Red No.104-1 (Phloxine), Food Red No.105-1 (Rose Bengale), Food Red No.106 (Acid Red), Food Yellow No.4 (Tartrazine), Food Yellow No.5 (Sunset Yellow FCF), Food Green No.3 (Fast Green FCF), Food Blue No.1 (Brilliant Blue FCF), Food Blue No.2 (Indigo Carmine) and the like, though they are not limited.

As the surfactants, can be mixed an anionic surfactant such as dioctyl sodium sulfosuccinate, alkylsulfate, 2-ethylhexyl alkyl sulfate sodium salt or sodium n-dodecyl benzenesulfonate, a cationic surfactant such as hexadecyl trimethylammonium chloride, octadecyl dimethyl benzyl ammonium chloride or polyoxyethlene dodecyl monomethylammonoum chloride, and a nonionic surfactant such as polyoxyethylene stearylether, polyoxyethylene tridecylether, polyoxyethylene nonylphenylether, polyoxyethylene, octylphenylether, polyoxyethylene monostearate, sorbitan monostearate, sorbitan monopalmitate, sorbitan sesquioleate, polyoxyethylene sorbitan monolaurate, polyoxyethylene sorbitan monooleate, glycerol monostearate, polyglycerin fatty acid ester or polyoxyethylene octadecyl amine.

As the UV absorbers can be mixed p-aminobenzoic acid, p-aminobenzoate, amyl p-dimethylaminobenzoate, salicilate, methyl anthranilate, umbelliferone, esculin, benzyl silicate, cinoxate, guaiazulene, urocainic acid, 2-(2-hydrozxy-5-methylphenyl)benzotriazole, 4-methoxybenzophenone, 2-hydroxy-4-methoxy benzophenone, dioxybenzone, octabenzone, dihydroxy dimethoxybenzophenone, slisobenzone, benzoresorcinol, octyl dimethyl p-aminobenzoate, ethylhexyl p-methoxycinnamate, and the like.

As the inorganic fillers, can be mixed titanium oxide, talc, zinc oxide, silicate hydrate, magnesium carbonate, dibasic calcium phosphate, magnesium silicate, diatomaceous earth, anhydrous silicic acid, bentonite and the like.

As the pH adjusting agents can be mixed acetic acid, formic acid, lactic acid, tartaric acid, oxalic acid, benzoic acid, glycolic acid, malic acid, citric acid, hydrochloric acid, nitric acid, sulfuric acid, sodium hydroxide, potassium hydroxide, methylamine, ethylamine, propylamine, dimethylamine, diethylamine, dipropylamine, trimethylamine, triethylamine, tripropylamine, monomethanolamine, monoethanolamine, monopropanolamine, dimethanolamine, diethanolamine, diprpopanolamine, trimethanolamine, triethanolamine, tripropanolamine and the like.

The pH of an adhesive mass appropriately mixed in a suitable amount of each of the above components is to be considered not to give irritancy to the skin, preferably in the range of 5–8, more preferably 5.5–7.5, furthermore preferably 6–7.

Further, illustrative of a backing on which an adhesive mass is applied is a flexuous one such as a synthetic resin film of polyethylene, polypropylene, polyethylene terephthalate, ethylene-vinylacetate copolymer, vinyl chloride, polyurethane, polyester, polyamide, rayon or the like, a base fabric such as elastic nonwoven-fabric, nonwoven paper, laminate of elastic nonwoven-fabric or nonwoven paper with the above synthetic resin film or sheet, absorbent cotton or the like, cloth, elastic cloth, paper, cellophane or the like, and those known to a person skilled in the art can appropriately be selected according to the application. Further, a pack layer is applied on the base fabric consisting of a flexuous backing and the surface of this pack layer is covered further with a removable film or paper, whereby the stability of the preparation can be kept. Also, in order to make it easy to apply a pack to the face, a separation line, perforating or the like can be set on the removal paper to make a form which is easy to separate. Furthermore, the color of a base fabric is not particularly limited, though owing to the fact that it greatly affects an image of a preparation and provides usability and feeling of an activated skin in a greater degree, white, skin color, yellow, red, orange, green, blue,, pink, light blue, brown or the like can be cited, and if necessary a shade is preferably adjusted.

In a process for preparing a sheet-shaped pack agent of the invention, the above components are uniformly mixed and/or dissolved in a stirring machine and spreaded on a base fabric of non-dyeing or dyeing, thereon a removable paper is stuck, and it is cut in a shape of the face. Further, parts for eye, nose, mouth and tin are cut in an appropriate shape, whereby it is processed for the convenience of handling. Also, aiming to use in a part of face, it can be processed into a shape to apply well to an aimed part as a nose pack which is applied to nose or an eye-around pack which is applied to around eye. Further, a sheet-shaped pack agent is desirably preserved in a sealed bag or container until use from the view point that contamination under preservation, the decrease of effectiveness by the evaporation of a volatile substance, or the like are prevented.

In a sheet-shaped pack agent of the invention, vitamin C, α-hydroxy acid, or other vitamins contained in the fruit extract act on the skin to activate the skin, and it shows such an excellent effect that its good water holding capacity gives a soft touch to the skin and has fragrance to soften a feeling to make relax. Particularly, a sheet-shaped pack agent in which the moisturising agent in a combination of the glycol and the fruit extract is excellent in adhesiveness and agglutinativeness of the preparation, a water holding capacity and a shape retaining property before use, does not show irritancy to the skin during use, and is extremely excellent in usability never met before. Further, a sheet-shaped pack agent which makes the water-soluble polymer, the cross-linking agent, water and the antiseptic as main components in addition to this moisturising agent is excellent in adhesiveness and agglutinativeness, a water holding capacity and a shape retaining property before use, and is particularly expedient as a sheet-shaped pack agent which is a soft to the skin and excellent in a beauty-skin action.

In the following, the sheet-shaped pack agent of the invention is explained in more detail by the examples and the test examples. However, the invention is not limited in any way by these.

EXAMPLE 1

Synthetic aluminum silicate 4 wt. % is dispersed in purified water 78.6 wt. %. This is added with gelatin 1 wt. %, ethyleneglycol diglycidyl ether 0.05 wt. %, grapefruit extract 0.045 wt. %, apple extract 0.045 wt. %, orange juice 0.003 wt. %, lemon juice 0.002 wt. %, lime juice 0.005 wt. % and methylparaben 0.2 wt. %, and the mixture is dissolved, further added with the mixture of sodium polyacrylate 6 wt. %, polyethylene glycol 10 wt. % and propylparaben 0.05 wt. % and stirred till these become homogeneous. Subsequently, the mixture is spreaded on a base fabric dyed into a pale orange color to make thickness about 1.4 mm and is stuck with film. Further, after the sticking, it is cut in a shape of the face, and parts of eyes, nose, mouth and tin are cut in an appropriate shape to afford the sheet-shaped pack agent.

EXAMPLES 2–20

The preparation in the same way as the example 1 using the mix agents and the mix amounts shown in Table 1, Table 2 and Table 3 afforded the sheet-shaped pack agent.

TABLE 1

| Components (%) | Examples |  |  |  |  |  |  |  |
|---|---|---|---|---|---|---|---|---|
|  | 2 | 3 | 4 | 5 | 6 | 7 | 8 | 9 |
| Fruit extracts |  |  |  |  |  |  |  |  |
| Grapefruit extract |  | 5 | 3 |  | 0.3 |  |  | 0.1 |
| Rapsberry extract |  |  |  |  |  |  |  |  |
| Apple extract | 0.01 | 10 | 15 |  |  |  |  |  |
| Apple juice |  |  |  |  |  |  |  |  |
| Orange extract |  |  |  |  |  | 5 |  |  |
| Orange juice |  | 5 | 2 |  | 0.2 | 5 |  |  |
| Grape extract |  |  |  |  |  |  |  |  |
| Lemon extract |  |  |  |  | 0.3 |  |  |  |
| Lemon juice |  |  |  | 5 | 15 |  |  |  |
| Lime juice |  |  |  | 5 | 10 | 0.2 |  | 0.05 |
| Density | 1.10 | 1.06 | 1.02 | 0.98 | 1.01 | 1.20 | 0.99 | 1.01 |
| pH (1→10) | 5.0 | 4.2 | 4.7 | 3.3 | 3.4 | 4.3 | 3.5 | 4.0 |
| Sugar content (wt %) | 21 | 23 | 23 | 20 | 21 | 22 | 19 | 19 |
| Polyethylene glycol | 25 | 5 |  |  | 15 | 5 |  | 5 |
| Polypropylene glycol | 10 |  | 1 | 5 | 10 | 10 | 3 |  |
| Gelatin | 3 | 5 | 4 | 0.9 | 1 | 0.5 |  | 10 |
| Sodium polyacrylate |  | 5 | 3 | 4 | 6 | 7 | 5 | 15 |
| Kaolin |  | 5 |  |  |  |  | 15 |  |
| Aluminum, acetate |  |  | 0.5 |  |  |  |  |  |
| Synthetic aluminum silicate |  |  |  |  | 3 | 5 | 4 |  |
| Sorbitol polyglycidyl ether | 0.05 |  |  | 0.01 |  |  |  |  |
| Polyethylene glycol diglycidyl ether |  |  |  | 0.01 | 0.1 |  | 0.25 |  |
| Propylene glycol diglycidyl ether |  |  | 0.3 |  |  |  |  |  |
| Glycerin diglycidyl ether |  | 0.01 |  | 0.02 |  |  | 0.5 |  |
| Polyglycerol polyglycidyl ether |  |  | 0.2 |  |  |  |  |  |
| Glycerin triglycidyl ether |  |  |  | 0.01 |  |  | 0.25 | 0.5 |
| Methylparaben |  |  | 1 |  | 0.1 |  | 9.9 | 4.5 |
| Ethylparaben | 0.01 |  |  |  | 0.1 | 0.1 |  | 0.5 |
| Propylparaben |  | 0.005 |  | 0.01 | 0.1 | 0.05 | 0.1 |  |
| Perfume |  | 0.001 |  | 0.01 |  |  |  |  |
| Water | 61.9 | 60 | 60 | 65 | 63.6 | 62.4 | 62 | 64.4 |
| Base fabric (dyeing) | Pale red | Non dyeing | Pink | Pale green | Non dyeing | Orange | Green | Yellow |

TABLE 2

| Components (%) | Examples |  |  |  |  |  |  |  |
|---|---|---|---|---|---|---|---|---|
|  | 10 | 11 | 12 | 13 | 14 | 15 | 16 | 17 |
| Fruit extracts |  |  |  |  |  |  |  |  |
| Grapefruit extract | 0.6 | 0.1 |  |  |  |  | 0.001 | 1 |
| Rapsberry extract |  |  |  |  |  | 1 | 0.002 |  |
| Apple extract | 1 | 0.1 |  | 0.05 |  |  | 0.001 | 5 |
| Apple juice |  |  |  |  |  | 0.5 | 0.005 |  |
| Orange extract |  |  |  |  |  |  |  |  |
| Orange juice |  | 0.1 |  | 0.05 |  |  |  | 1 |
| Grape extract |  |  |  |  | 0.01 |  | 0.001 |  |
| Lemon extract |  |  |  |  |  |  |  | 2 |
| Lemon juice | 0.02 | 0.1 | 0.01 |  |  |  |  |  |
| Lime juice |  | 0.1 |  |  |  |  |  |  |
| Density | 1.11 | 1.02 | 0.95 | 1.09 | 1.10 | 0.99 | 1.01 | 1.07 |
| pH (1→10) | 4.2 | 3.6 | 3.4 | 4.6 | 4.4 | 4.0 | 3.9 | 4.8 |

TABLE 2-continued

| Components (%) | Examples |  |  |  |  |  |  |  |
|---|---|---|---|---|---|---|---|---|
|  | 10 | 11 | 12 | 13 | 14 | 15 | 16 | 17 |
| Sugar content (wt %) | 19 | 21 | 20 | 22 | 23 | 22 | 21 | 23 |
| Polyethylene glycol | 15 |  | 3 |  | 15 | 5 |  | 7 |
| Polypropylene glycol | 5 | 10 | 1 | 1 |  |  | 2 | 3 |
| Gelatin | 2 | 0.3 | 2.5 | 3 | 10 |  | 3 | 1 |
| Sodium polyacrylate | 6 | 4 | 1 |  | 10 | 8 |  | 6 |
| Kaolin |  |  | 1 |  |  | 8 | 10 |  |
| Aluminum, acetate |  |  |  |  | 0.01 | 2 | 2 |  |
| Synthetic aluminum silicate |  | 0.05 | 1 |  |  |  | 1 | 4 |
| Sorbitol polyglycidyl ether |  |  |  |  |  |  | 0.3 |  |
| Polyethylene glycol diglycidyl ether |  | 0.05 |  | 0.4 |  |  | 0.2 |  |
| Propyleneglycoldiglycidyl ether |  |  |  |  | 0.1 |  | 0.25 |  |
| Glycerin diglycidyl ether |  |  |  |  |  |  | 0.5 |  |
| Polyglycerol polyglycidyl ether |  |  |  |  |  |  | 0.5 | 0.05 |
| Glycerin triglycidyl ether | 0.08 |  | 0.1 |  |  |  | 0.25 |  |
| Methylparaben | 0.3 |  |  | 0.5 | 0.3 |  | 0.1 |  |
| Ethylparaben |  |  |  |  |  | 0.5 |  | 0.1 |
| Propylparaben |  | 0.1 | 0.4 |  |  |  | 0.04 | 0.05 |
| Perfume |  |  |  |  |  |  |  | 0.005 |
| Water | 70 | 85 | 90 | 95 | 64.6 | 75 | 80 | 68.7 |
| Base fabric (dyeing) | White | Skin color | Pale yellow | Light blue | Non dyeing | Non dyeing | Non dyeing | Non dyeing |

TABLE 3

| Components (%) | Examples |  |  |
|---|---|---|---|
|  | 18 | 19 | 20 |
| Fruit extracts |  |  |  |
| Grapefruit extract |  | 3.5 |  |
| Rapsberry extract |  |  |  |
| Apple extract |  | 13.5 |  |
| Apple juice |  |  |  |
| Orange extract | 0.005 |  |  |
| Orange juice |  | 3.5 |  |
| Grape extract |  |  | 0.005 |
| Lemon extract |  | 7 |  |
| Lemon juice |  |  |  |
| Lime juice |  | 3.5 |  |
| Density | 1.16 | 1.03 | 1.10 |
| pH (1→10) | 4.3 | 4.5 | 4.4 |
| Sugar content (wt %) | 22 | 22 | 23 |
| Polyethylene glycol |  | 0.5 | 20 |
| Polypropylene glycol | 0.5 |  | 16 |
| Gelatin | 10 | 7 |  |
| Sodium polyacrylate |  |  | 3.7 |
| Kaolin |  |  |  |
| Aluminum, acetate |  |  |  |
| Synthetic aluminum silicate | 3 |  |  |
| Sorbitol polyglycidyl ether |  |  | 0.01 |
| Polyethylene glycol diglycidyl ether |  |  |  |
| Propylene glycol diglycidyl ether |  |  | 0.04 |
| Glycerin diglycidyl ether |  |  |  |
| Polyglycerol polyglycidyl ether |  | 1 |  |
| Glycerin triglycidyl ether | 1 |  |  |
| Methylparaben | 0.5 | 0.5 | 0.25 |
| Ethylparaben |  |  |  |
| Propylparaben |  |  |  |
| Perfume |  |  |  |
| Water | 85 | 60 | 60 |
| Base fabric (dyeing) | Non dyeing | Non dyeing | Non dyeing |

Comparative Example 1

The example 1 in JP, A, H8-188527 filed previously was made the comparative example, and in the following test examples it was compared with the examples.

Synthetic aluminum silicate 4 wt. % is dispersed in purified water 76.5 wt. %. This is added with gelatin 1 wt. %, 2% Succinyl Kefinran aq. 0.1 wt. %, ethyleneglycol diglycidyl ether in 0.05 wt. %, water soluble placenta extract 2 wt. %, allantoin 0.1 wt. % and methylparaben 0.2 wt. %, and the mixture is dissolved, further added with the mixture of sodium polyacrylate 6 wt. %, polyethylene glycol 10 wt. % and propylparaben 0.05 wt. % and stirred till these become homogeneous. Subsequently, the mixture is spreaded on a base fabric dyed into a pale blue color to make thickness about 1.4 mm and is stuck with film. Further, after the sticking, it is cut in a shape of the face, and parts of eyes, nose, mouth and tin are cut in an appropriate shape to afford the sheet-shaped pack agent.

Test Example 1

Adhesiveness Test

As for the examples 1, 6, 11, 18, 19 and 20 the results of the adhesiveness test are shown in Table 4. In the test was used the samples which were let stand in advance for not less than 30 min. under the condition of 25° C.–60% Rh, and the test was carried out under the same condition. First, the sticking part of the sample was fixed on a horizontal stand in the upward direction. Subsequently, steel ball whose diameter was 20/32 inch was dropped from the height of 17.35 cm for the length of 30 cm on the base agent in the sine curve and was rolled on the sticky surface. Here, the distance (cm) from the ground point of the steel ball to the reaching point was evaluated as the stick strength. Further, the material of the steel ball used was SUJ2 of JIS G4805 (High Carbon chromium Bearing Steels) and its precision was the upper class of JIS B1501 (Steel Ball for Ball Bearings).

TABLE 4

|  | Adhesive strength |
| --- | --- |
| Example 1 | 3 cm |
| Example 6 | 2 cm |
| Example 11 | 5 cm |
| Example 18 | 13 cm |
| Example 19 | 10 cm |
| Example 20 | 15 cm |

Test Example 2

Residual Test of Water Content and Oil Content on Skin Surface

As for the examples 3, 10 and 13, the water content and the oil content on the skin surface was measured before use and after use, and the results in which the comparison was each made are shown in Table 5. After subjects were restricted for not less than 30 min. under the condition of 25° C.–60% Rh, the water content of the cheek and the oil content of the forehead were measured using SKICOS 301 (manufactured by AMIQUE GROUP CO., LTD.) in the test. Subsequently, after the samples cut into 3 cm×3 cm were stuck on the cheek and the forehead of the subjects for 15 min., the water content of the cheek and the oil content of the forehead was measured likewise.

TABLE 5

|  | Water content ($mg\ H_2O/cm^2$) | | Oil content ($Mg/cm^2$) | |
| --- | --- | --- | --- | --- |
|  | Before use | After use | Before use | After use |
| Example 3 | 50 | 103 | 72 | 19 |
| Example 10 | 54 | 110 | 82 | 25 |
| Example 13 | 51 | 120 | 65 | 14 |

Test Example 3

Usability Evaluation Test

As for the example 1 and the comparative example 1 the usability test was carried out. In the test, to 50 persons of women in the age of twenties were donated both samples of the example 1 and the comparative example 1 with each one sheet for each person, and each sheet was let be used in a different day. Later, the evaluation was made in 5 degrees on "well absorbing feeling", "efficiency penetrating feeling" and "relaxant feeling". The results are shown in Table 6 (well absorbing feeling), in Table 7 (efficacy penetrating feeling) and in Table 8 (relaxant feeling).

TABLE 6

(a well absorbing feeling) (% representation)

|  | very good | good | not definite | not very good | not good |
| --- | --- | --- | --- | --- | --- |
| Example 1 | 18 | 60 | 10 | 12 | 0 |
| Comparative Example 1 | 14 | 68 | 10 | 8 | 0 |

TABLE 7

(efficacy penetrating feeling) (% representation)

|  | very good | good | not definite | not very good | not good |
| --- | --- | --- | --- | --- | --- |
| Example 1 | 16 | 42 | 26 | 14 | 0 |
| Comparative Example 1 | 8 | 56 | 22 | 12 | 2 |

TABLE 8

(relaxant feeling) (% representation)

|  | very good | good | not definite | not very good | not good |
| --- | --- | --- | --- | --- | --- |
| Example 1 | 48 | 46 | 4 | 2 | 0 |
| Comparative Example 1 | 40 | 46 | 10 | 4 | 0 |

Test Example 4

Skin Safety Test

As for the examples 1, 2, 4, 7 and 17, and the comparative example 1, the skin safety test was carried out. The 48 hrs. closed patch test was carried out for 30 persons of healthy men and women. Changes of the skin were observed after 1 hr. and 24 hrs. from the removal, and the irritancy degree of the skin was evaluated according to the below standards. The results are shown in Table 9.

−: No change is observed in the skin
±: Faint flare in the skin
+: Clear flare in the skin
++: Severe feeling in the skin

TABLE 9

| Time after removal | Judgement Samples | ++ | + | ± | − | Total (person) | Positive ratio (%) Not less than ± |
| --- | --- | --- | --- | --- | --- | --- | --- |
| After 1 hr. | Example 1 | 0 | 0 | 0 | 30 | 30 | 0.0 |
|  | Example 2 | 0 | 0 | 1 | 29 | 30 | 3.3 |
|  | Example 4 | 0 | 0 | 2 | 28 | 30 | 6.7 |
|  | Example 7 | 0 | 0 | 0 | 30 | 30 | 0.0 |
|  | Example 17 | 0 | 0 | 1 | 29 | 30 | 3.3 |
|  | Comparative Example 1 | 0 | 0 | 4 | 26 | 30 | 13.3 |
| After 24 hr. | Example 1 | 0 | 0 | 0 | 30 | 30 | 0.0 |
|  | Example 2 | 0 | 0 | 0 | 30 | 30 | 0.0 |
|  | Example 4 | 0 | 0 | 0 | 30 | 30 | 0.0 |
|  | Example 7 | 0 | 0 | 0 | 30 | 30 | 0.0 |
|  | Example 17 | 0 | 0 | 0 | 30 | 30 | 0.0 |
|  | Comparative Example 1 | 0 | 0 | 1 | 29 | 30 | 3.3 |

As described above, it was found that the sheet-shaped pack agent of the invention had a moderate stickiness and was good in usability and excellent in the safety for the skin. It was also found that the effect to the skin and the relaxant effect by the fruit components were excellent.

FIELD OF INDUSTRIAL APPLICATION

In the sheet-shaped pack according to the present invention, the vitamin C, α-hydroxylic acid or other vitamins contained by fruit extracts activate the skin to bring a nice feeling and a relaxant effect by a soft aroma due to the excellent water holding capacity.

In particular, the sheet-shaped pack agent using moisturising agents consisting of two components of the glycol and the first extract exhibits an excellent adhesiveness and agglutinativeness of the preparation, an excellent water holding capacity and shape retaining property before use, workability, usability at the use, and a low irritancy to the skin.

The sheet-shaped pack agent comprising, in addition to moisturising agent, water soluble polymer, cross-linking agent, water and antiseptic are especially preferable.

Accordingly, the sheet-shaped pack agent of the invention is easy to handle and is excellent in terms of the safety, usability and effect to the skin; therefore it is suitable for the application in the field of quasi-drug or cosmetics used for a skindressing and beauty, and thus, very useful industrially.

What is claimed is:

1. A sheet-shaped pack agent comprising a base agent containing 60–95 wt. % of water a moisturizing agent and a fruit extract whose density is 0.95–1.20, the pH is 3.3–5.0 and the sugar content is 19–23 wt. %.

2. The sheet-shaped pack agent according to claim 1, characterized in that it comprises a base fabric and a base agent.

3. The sheet-shaped pack agent according to claim 1, characterized in that the mixing proportion of the fruit extract in a total amount of a base agent is 0.0003–33.87 wt. %.

4. The sheet-shaped pack agent according to claim 3, characterized in that the proportion of the fruit extract in a total amount of a moisturising agent is 0.03–96.77 wt. %.

5. The sheet-shaped pack agent according to claims 3 or 4, characterized in that the base agent contains a moisturizing agent 1–35 wt. %, a water soluble polymer 3–25 wt. %, and a cross-linking agent 0.05–20 wt. %.

6. The sheet-shaped pack agent according to claim 5, characterized in that the base agent further contains an antiseptic 0.005–10 wt. %.

7. The sheet-shaped pack agent according to claim 1, further comprising a glycol.

8. The sheet-shaped pack agent according to claim 7, characterized in that the mix ratio of the glycol to the fruit extract is 1–35:0.01–30.

9. The sheet-shaped pack agent according to claim 7, characterized in that the glycol is polyethylene glycol and/or polypropylene glycol.

10. The sheet-shaped pack agent according to claim 1, characterized in that the fruit extract comprises one or more species selected from the group consisting of rose fruit extract, orange extract, orange juice, raspberry extract, kiwi extract, cucumber extract, gardenia extract, grapefruit extract, crataegus fruit extract, Japanese pepper extract, crataegus extract, common juniper extract, jujube extract, duke extract, tomato extract, grape extract, lime juice, apple extract, apple juice, lemon extract and lemon juice.

11. The sheet-shaped pack agent according to claim 1, constructed and arranged for use in cosmetics for the skin or delivery of a quasi-drug.

* * * * *

UNITED STATES PATENT AND TRADEMARK OFFICE
CERTIFICATE OF CORRECTION

PATENT NO. : 7,045,137 B1
APPLICATION NO. : 09/890224
DATED : May 16, 2006
INVENTOR(S) : Kazunori Muta et al.

it is certified that error appears in the above-identified patent and that said Letters Patent is hereby corrected as shown below:

In the specification, column 1, line 66, please delete the word "inventory" and replace it with the word -- invention --;

In the specification, column 2, line 2, please delete "1.35" and replace it with -- 1-35 --;

In the specification, column 3, line 11, please delete "0.01.25" and replace it with -- 0.01-25 --;

In the specification, column 3, line 17, please delete "2.0" and replace it with -- 20 --;

In the specification, column 3, line 33, please delete "3.25" and replace it with -- 3-25 --;

In the specification, column 4, line 43, please delete the word "methylphenyl" and replace it with the word -- methylphenol --;

In the specification, column 4, line 57, please delete the word "methanol" and replace it with the word -- menthol --;

In the specification, column 5, line 10, please delete the word "mirystate" and replace it with the word -- myristate --;

In the specification, column 5, line 29, please delete the word "ethylammonoum" and replace it with the word -- ethylammonium --;

In the specification, column 5, line 32, please delete the comma after the word "polyoxyethylene";

In the specification, column 5, line 42, please delete the word "hydrozxy" and replace it with the word -- hydroxy --;

In the specification, column 5, line 61, please delete the word "diprpopanolamine" and replace it with the word -- dipropanolamine --;

In the specification, column 6, line 24, please delete the duplicate comma after the word "blue";

In the specification, column 10, in "Table 2-continued," please move "0.1" from column 16 to column 17 within Table 2;

UNITED STATES PATENT AND TRADEMARK OFFICE
CERTIFICATE OF CORRECTION

PATENT NO. : 7,045,137 B1
APPLICATION NO. : 09/890224
DATED : May 16, 2006
INVENTOR(S) : Kazunori Muta et al.

it is certified that error appears in the above-identified patent and that said Letters Patent is hereby corrected as shown below:

In the specification, column 11, line 35, in Table 5, please delete "Mg" and replace it with -- µg --;

In the specification, column 11, line 53, please delete the word "efficiency" and replace it with the word -- efficacy --;

In the specification, column 12, line 7, in Table 7, please delete "16" and replace it with -- 18 --;

In the specification, column 13, line 3, please delete the word "first" and replace it with the word -- fruit --;

In claim 1, column 13, line 18, please add a comma after the word "water";

In claim 1, column 13, line 18, please delete the word "moisturizing" and replace it with the word -- moisturising --;

In claim 1, column 13, line 18, after the word "agent," please add the words -- that includes -- and delete the word "and";

In claim 5, column 14, line 2, please delete the word "moisturizing" and replace it with the word -- moisturising --;

Signed and Sealed this

Twenty-second Day of May, 2007

JON W. DUDAS
*Director of the United States Patent and Trademark Office*